(12) United States Patent
Guide

(10) Patent No.: US 11,850,300 B2
(45) Date of Patent: Dec. 26, 2023

(54) TOPICAL LOTION COMPOSITION, METHODS OF USE, AND METHODS OF PREPARATION

(71) Applicant: Rally Guide, Santa Ana, CA (US)

(72) Inventor: Rally Guide, Santa Ana, CA (US)

(*) Notice: Subject to any disclaimer, the term of this patent is extended or adjusted under 35 U.S.C. 154(b) by 0 days.

(21) Appl. No.: 17/696,981

(22) Filed: Mar. 17, 2022

(65) Prior Publication Data

US 2023/0293422 A1    Sep. 21, 2023

(51) Int. Cl.
| | |
|---|---|
| *A61K 8/92* | (2006.01) |
| *A61K 8/9789* | (2017.01) |
| *A61Q 7/00* | (2006.01) |
| *A61K 8/67* | (2006.01) |

(52) U.S. Cl.
CPC .............. *A61K 8/922* (2013.01); *A61K 8/678* (2013.01); *A61K 8/927* (2013.01); *A61K 8/9789* (2017.08); *A61Q 7/00* (2013.01); *A61K 2800/30* (2013.01); *A61K 2800/5922* (2013.01); *A61K 2800/805* (2013.01)

(58) Field of Classification Search
None
See application file for complete search history.

(56) References Cited

U.S. PATENT DOCUMENTS

| | | | |
|---|---|---|---|
| 8,298,592 B2 | 10/2012 | Nam | |
| 8,541,466 B2 | 9/2013 | DeLong | |
| 9,750,812 B2 | 9/2017 | Ali | |
| 9,839,606 B2 | 12/2017 | Alhallami | |
| 10,238,596 B1 * | 3/2019 | Peck | A61K 8/737 |
| D920,127 S | 5/2021 | Allan | |
| 2014/0322148 A1 | 10/2014 | Jackson | |
| 2020/0147071 A1 | 5/2020 | Jindal | |
| 2020/0352849 A1 | 11/2020 | Rotunda | |

FOREIGN PATENT DOCUMENTS

| | | | |
|---|---|---|---|
| TR | 202017808 A2 * | 1/2021 | |
| WO | WO2010036947 | 4/2010 | |

* cited by examiner

*Primary Examiner* — Nannette Holloman

(57) ABSTRACT

A topical lotion composition for promoting hair growth includes honey, *Aloe vera* gel, rosemary oil, coconut oil, olive oil, rose oil, almond oil, and vitamin E oil, in a base. Application of the topical lotion composition to a scalp of a user promotes hair growth.

17 Claims, 2 Drawing Sheets

TOPICAL LOTION COMPOSITION, METHODS OF USE, AND METHODS OF PREPARATION

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to lotion compositions and more particularly pertains to a new lotion composition for promoting hair growth. The present invention discloses a lotion composition comprising honey, coconut oil, olive oil, almond oil, and one or more of rose oil, *Aloe vera* gel, rosemary oil, and vitamin E oil, in a base, wherein the lotion composition is effective in promoting hair growth.

(2) Description of Related Art Including Information Disclosed Under 37 CFR 1.97 and 1.98

The prior art relates to lotion compositions, and in particular lotion compositions for promoting hair growth. Such prior art lotion compositions may comprise honey in combination with one or more of coconut oil, olive oil, almond oil. What is lacking in the prior art is a lotion composition comprising honey, coconut oil, olive oil, almond oil, and one or more of rose oil, *Aloe vera* gel, rosemary oil, and vitamin E oil, in a base.

BRIEF SUMMARY OF THE INVENTION

An embodiment of the disclosure meets the needs presented above by generally comprising honey, *Aloe vera* gel, rosemary oil, coconut oil, olive oil, rose oil, almond oil, and vitamin E oil, in a base. The topical lotion composition is configured for application a scalp of a user to promote hair growth.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

DETAILED DESCRIPTION OF THE INVENTION

A new lotion composition embodying the principles and concepts of an embodiment of the disclosure will be described. The topical lotion composition generally comprises honey, coconut oil, olive oil, almond oil, and one or more of rose oil, *Aloe vera* gel, rosemary oil, and vitamin E oil, in a base. The topical lotion composition is configured for application a scalp of a user to promote hair growth. The topical lotion composition may comprise honey, coconut oil, olive oil, almond oil, rose oil, *Aloe vera* gel, rosemary oil, and vitamin E oil, in a base.

The topical lotion composition may comprise, on a volume/volume basis, 2.50 to 7.50% honey, 5.00 to 10.00% *Aloe vera* gel, 1.00 to 2.00% rosemary oil, 1.00 to 2.00% coconut oil, 0.50 to 1.25% olive oil, 0.50 to 1.25% rose oil, 2.00 to 3.00% almond oil, 0.25 to 0.75% vitamin E oil, and 72.25 to 86.00% of the base. The topical lotion composition may comprise, on a volume/volume basis, 4.50 to 5.00% honey, 7.00 to 8.00% *Aloe vera* gel, 1.50 to 1.75% rosemary oil, 1.50 to 1.75% coconut oil, 0.60 to 0.80% olive oil, 0.60 to 0.80% rose oil, 2.25 to 2.50% almond oil, 0.30 to 0.50% vitamin E oil, and 78.90 to 81.75% of the base.

The topical lotion composition the also may comprise one or both of cactus gel and bergamot oil. For example, the topical lotion composition may comprise, on a volume/volume basis, one or both of cactus gel at 2.50 to 7.50% and bergamot oil at 0.50 to 1.25%, with the base comprising 69.25 to 77.25% of the topical lotion composition.

The topical lotion composition is devoid of mineral oil and paraffins. The base comprises one or more of water, sunflower seed oil, glycerin, coconut oil, safflower seed oil, soybean oil, canola oil, grape seed oil, glycerin, glyceryl stearate, glyceryl stearate citrate, glyceryl caprylate, ethylhexylglycerin, polyglyceryl-3 polyricinoleate, betaine, shea butter, tapioca starch, palmitic acid, isopropyl palmitate, lactic acid, citric acid, sorbitan olivate, xanthan gum, wool wax, beeswax, hydrolyzed beeswax, decyl cocoate, nonfat dry milk, stearic acid, sucrose stearate, sodium stearoyl lactylate, sodium benzoate, potassium sorbate, magnesium aluminum silicate, dimethicone, ethanol, cetyl alcohol, cetearyl alcohol, phenoxyethanol, benzyl alcohol, benzyl benzoate, polysorbate 20, carbomer, p-anisic acid, sodium hydroxide, titanium dioxide, and fragrance.

Figure 1:
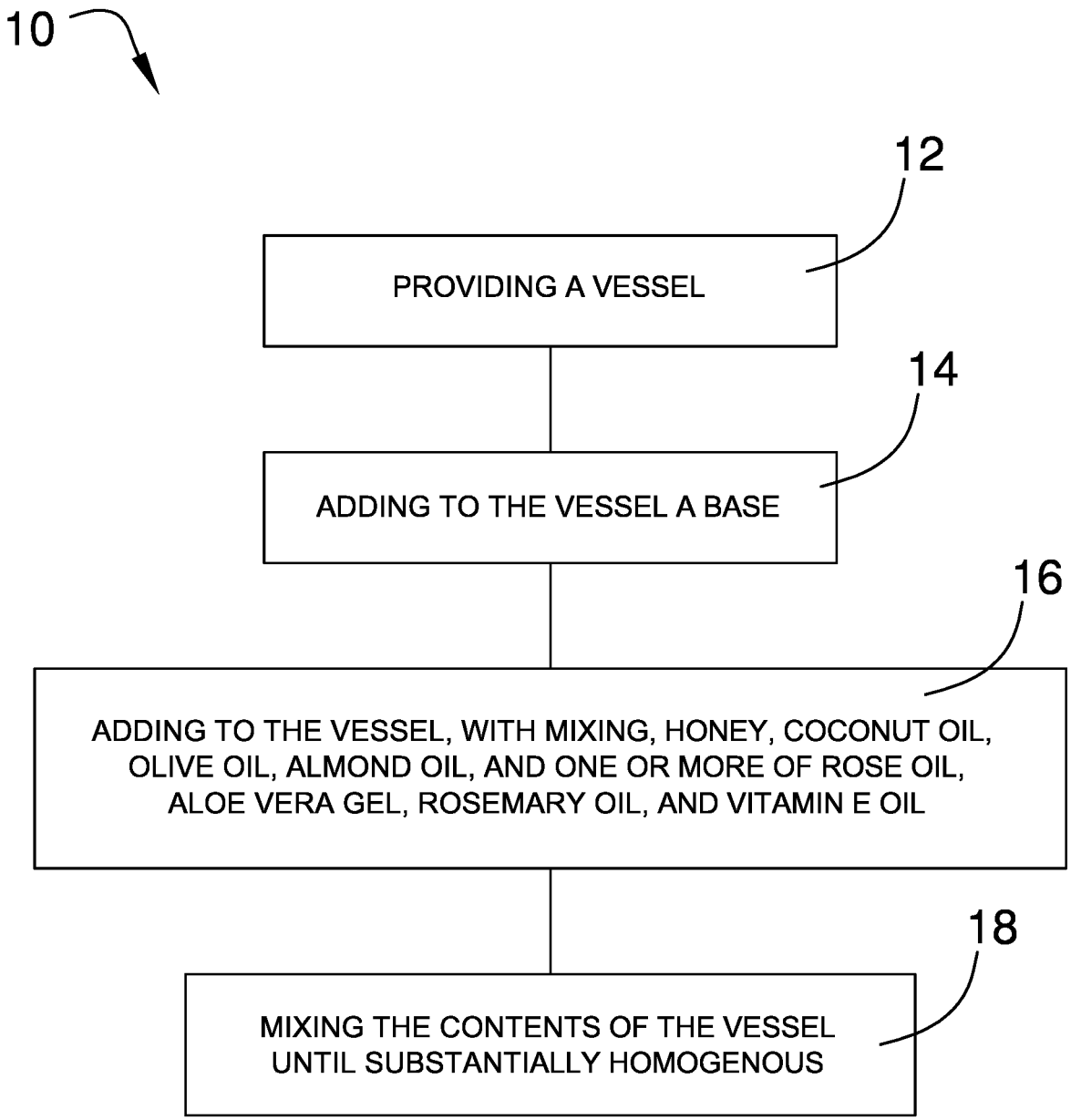
FIG. 1 is a flow diagram for a method of preparing a topical ointment composition according to an embodiment of the disclosure.

The present invention anticipates a method of preparing a topical lotion composition for use in promoting hair growth, as shown in FIG. 1. The preparation method 10 comprises a first step 12 providing a vessel. A second step 14 of the preparation method 10 is adding a base to the vessel. A third step 16 of the preparation method 10 is adding to the vessel, with mixing, honey, *Aloe vera* gel, rosemary oil, coconut oil, olive oil, rose oil, almond oil, and vitamin E oil. A fourth step 18 of the preparation method 10 is mixing the contents of the vessel until substantially homogenous.

For example, 500 mL of a base, such as, but not limited to, Johnson's® baby lotion, may be charged to the vessel. With stirring, 30 mL of honey, 45 mL of *Aloe vera* gel, 10 mL of rosemary oil, 10 mL of coconut oil, 5 mL of olive oil, 5 mL of rose oil, 15 mL of almond oil, and 2.5 mL of vitamin E oil are added to the base. Approximately 622 mL of the topical lotion composition is obtained comprising 80.32% base, 4.82% honey, 7.23% *Aloe vera* gel, 1.61% rosemary oil, 1.61% coconut oil, 0.80% olive oil, 0.80% rose oil, 2.41% almond oil, and 0.40% vitamin E oil.

Figure 2:
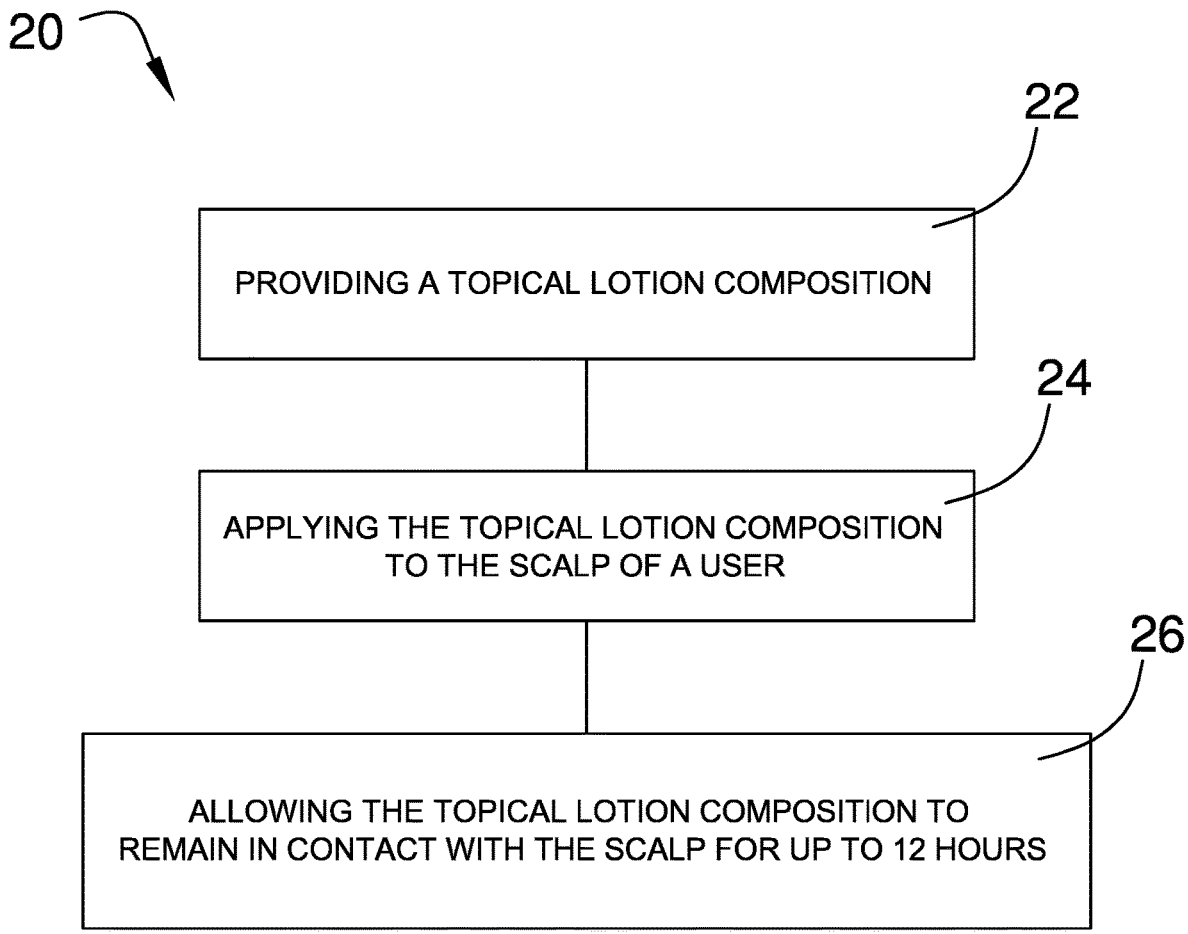
FIG. 2 is a flow diagram for a method of using an embodiment of the disclosure.

The topical lotion composition enables a method of promoting hair growth 20, as shown in FIG. 2. The hair growth method 20 comprises a first step 22 of providing a topical lotion composition according to the specification above. A second step 24 of the hair growth method 20 is applying the topical lotion composition to a scalp of a user. A third step 26 of the hair growth method 20 is allowing the topical lotion composition to remain in contact with the scalp for up to 12 hours. For example, the topical lotion composition may be allowed to remain in contact with the scalp between 1 and 8 hours.

Although the foregoing invention has been described in some detail by way of illustration and example for purposes of clarity and understanding, it will be readily apparent, in light of the teachings of this invention, that certain changes and modifications may be made thereto without departing from the spirit or scope of the following claims.

Therefore, the foregoing is considered as illustrative only of the principles of the disclosure. In this patent document, the word "comprising" is used in its non-limiting sense to mean that items following the word are included, but items not specifically mentioned are not excluded. A reference to an element by the indefinite article "a" does not exclude the possibility that more than one of the elements is present, unless the context clearly requires that there be only one of the elements.

I claim:

1. A topical lotion composition comprising honey, coconut oil, olive oil, almond oil, and one or more of rose oil, *Aloe vera* gel, rosemary oil, and vitamin E oil, in a base, wherein the topical lotion composition is configured for application a scalp of a user for promoting hair growth, wherein the topical lotion composition comprises, on a volume/volume basis, 2.50 to 7.50% honey, 5.00 to 10.00% *Aloe vera* gel 1.00 to 2.00% rosemary oil, 1.00 to 2.00% coconut oil, 0.50 to 1.25% olive oil, 0.50 to 1.25% rose oil, 2.00 to 3.00% almond oil, 0.25 to 0.75% vitamin E oil, and 72.25 to 86.00% of the base.

2. The topical lotion composition of claim 1, wherein the topical lotion composition comprises, on a volume/volume basis, 4.50 to 5.00% honey, 7.00 to 8.00% *Aloe vera* gel, 1.50 to 1.75% rosemary oil, 1.50 to 1.75% coconut oil, 0.60 to 0.80% olive oil, 0.60 to 0.80% rose oil, 2.25 to 2.50% almond oil, 0.30 to 0.50% vitamin E oil, and 78.90 to 81.75% of the base.

3. The topical lotion composition of claim 1, wherein the topical lotion composition is devoid of mineral oil and paraffins.

4. The topical lotion composition of claim 1, wherein the base comprises one or more of water, sunflower seed oil, glycerin, coconut oil, safflower seed oil, soybean oil, canola oil, grape seed oil, glycerin, glyceryl stearate, glyceryl stearate citrate, glyceryl caprylate, ethylhexylglycerin, polyglyceryl-3 polyricinoleate, betaine, rhea butter, tapioca starch, palmitic acid, isopropyl palmitate, lactic acid, citric acid, sorbitan olivate, xanthan gum, wool wax, beeswax, hydrolyzed beeswax, decyl cocoate, nonfat dry milk, stearic acid, sucrose stearate, sodium stearoyl lactylate, sodium benzoate, potassium sorbate, magnesium aluminum silicate, dimethicone, ethanol, cetyl alcohol, cetearyl alcohol, phenoxyethanol, benzyl alcohol, benzyl benzoate, polysorbate 20, carbomer, p-anisic acid, sodium hydroxide, titanium dioxide, and fragrance.

5. The topical lotion composition of claim 1, further including the topical lotion composition comprising one or both of cactus gel and bergamot oil.

6. The topical lotion composition of claim 1, further including:
the topical lotion composition comprising, on a volume/volume basis, one or both of cactus gel at 2.50 to 7.50% and bergamot oil at 0.50 to 1.25%; and
the base comprising 69.25 to 77.25% of the topical lotion composition.

7. A method of preparing a topical lotion composition for use in promoting hair growth, the method comprising the steps of:
providing a vessel;
adding to the vessel a base;
adding to the vessel, with mixing, honey, coconut oil, olive oil, almond oil, and one or more of rose oil, *Aloe vera* gel, rosemary oil, and vitamin E oil;
mixing the contents of the vessel until substantially homogenous; and
wherein the topical lotion composition comprises, on a volume/volume basis, 2.50 to 7.50% honey, 5.00 to 10.00% *Aloe vera* gel, 1.00 to 2.00% rosemary oil, 1.00 to 2.00% coconut oil, 0.50 to 1.25% olive oil, 0.50 to 1.25% rose oil, 2.00 to 3.00% almond oil, 0.25 to 0.75% vitamin E oil, and 72.25 to 86.00% of the base.

8. The preparation method of claim 7, wherein the topical lotion composition comprises, on a volume/volume basis, 4.50 to 5.00% honey, 7.00 to 8.00% *Aloe vera* gel, 1.50 to 1.75% rosemary oil, 1.50 to 1.75% coconut oil, 0.60 to 0.80% olive oil, 0.60 to 0.80% rose oil, 2.25 to 2.50% almond oil, 0.30 to 0.50% vitamin E oil, and 78.90 to 81.75% of the base.

9. The preparation method of claim 7, wherein the topical lotion composition is devoid of mineral oil and paraffins.

10. The preparation method of claim 7, wherein the base comprises one or more of water, sunflower seed oil, glycerin, coconut oil, safflower seed oil, soybean oil, canola oil, grape seed oil, glycerin, glyceryl stearate, glyceryl stearate citrate, glyceryl caprylate, ethylhexylglycerin, polyglyceryl-3 polyricinoleate, betaine, rhea butter, tapioca starch, palmitic acid, isopropyl palmitate, lactic acid, citric acid, sorbitan xanthan gum, wool wax, beeswax, hydrolyzed beeswax, decyl cocoate, nonfat dry milk, stearic acid, sucrose stearate, sodium stearoyl lactylate, sodium benzoate, potassium sorbate, magnesium aluminum silicate, dimethicone, ethanol, cetyl alcohol, cetearyl alcohol, phenoxyethanol, benzyl alcohol, benzyl benzoate, polysorbate 20, carbomer, p-anisic acid, sodium hydroxide, titanium dioxide, and fragrance.

11. The preparation method of preparation claim 7, further including the topical lotion composition comprising one or both of cactus gel and bergamot oil.

12. The preparation method of claim 7, further including:
the topical lotion composition, on a volume/volume basis, comprising one or both of cactus gel at 2.50 to 7.50% and bergamot oil at 0.50 to 1.25%; and
the base comprising 69.25 to 77.25% of the topical lotion composition.

13. A method of promoting hair growth utilizing a topical lotion composition, the method comprising the steps of:
providing a topical lotion composition comprising honey, coconut oil, olive oil, almond oil, and one or more of rose oil, *Aloe vera* gel, rosemary oil, and vitamin E oil, in a base;
applying the topical lotion composition to a scalp of a user;
allowing the topical lotion composition to remain in contact with the scalp for up to 12 hours; and
wherein the topical lotion composition comprises, on a volume/volume basis, 2.50 to 7.50% honey, 5.00 to 10.00% *Aloe vera* gel, 1.00 to 2.00% rosemary oil, 1.00 to 2.00% coconut oil, 0.50 to 1.25% olive oil, 0.50 to 1.25% rose oil, 2.00 to 3.00% almond oil, 0.25 to 0.75% vitamin E oil, and 72.25 to 86.00% of the base.

14. The hair growth method of claim 13, wherein the topical lotion composition is allowed to remain in contact with the scalp between 1 and 8 hours.

15. The hair growth method of claim 13, wherein:
the topical lotion composition is devoid of mineral oil and paraffins; and
the base comprises one or more of water, sunflower seed oil, glycerin, coconut oil, safflower seed oil, soybean oil, canola oil, grape seed oil, glycerin, glyceryl stearate, glyceryl stearate citrate, glyceryl caprylate, ethylhexylglycerin, polyglyceryl-3 polyricinoleate, betaine, shed butter, tapioca starch, palmitic acid, isopropyl palmitate, lactic acid, citric acid, sorbitan olivate, xanthan gum, wool wax, beeswax, hydrolyzed beeswax, decyl cocoate, nonfat dry milk, stearic acid, sucrose stearate, sodium stearoyl lactylate, sodium benzoate, potassium sorbate, magnesium aluminum silicate, dimethicone, ethanol, cetyl alcohol, cetearyl alcohol, phenoxyethanol, benzyl alcohol, benzyl benzoate, polysorbate 20, carbomer, p-anisic acid, sodium hydroxide, titanium dioxide, and fragrance.

16. The hair growth method of claim 13, further including the topical lotion composition comprising one or both of cactus gel and bergamot oil.

17. The hair growth method of claim 13, further including:
the topical lotion composition comprising, on a volume/volume basis, one or both of cactus gel at 2.50 to 7.50% and bergamot oil at 0.50 to 1.25%; and
the base comprising 69.25 to 77.25% of the topical lotion composition.

* * * * *